(12) United States Patent
Pacheco et al.

(10) Patent No.: US 9,724,493 B2
(45) Date of Patent: Aug. 8, 2017

(54) COMPONENTS AND METHODS FOR BALANCING A CATHETER CONTROLLER SYSTEM WITH A COUNTERWEIGHT

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US)

(73) Assignee: CATHETER PRECISION, INC., Ledgewood, NJ (US)

( * ) Notice: Subject to any disclaimer, the term of this patent is extended or adjusted under 35 U.S.C. 154(b) by 303 days.

(21) Appl. No.: 14/468,437

(22) Filed: Aug. 26, 2014

(65) Prior Publication Data
US 2015/0066052 A1   Mar. 5, 2015

Related U.S. Application Data

(60) Provisional application No. 61/870,311, filed on Aug. 27, 2013.

(51) Int. Cl.
*A61M 25/01* (2006.01)
*A61B 90/50* (2016.01)
*A61B 90/00* (2016.01)
*A61B 34/30* (2016.01)

(52) U.S. Cl.
CPC ......... *A61M 25/0113* (2013.01); *A61B 34/30* (2016.02); *A61B 2034/301* (2016.02);
(Continued)

(58) Field of Classification Search
CPC ................ A61B 19/22; A61B 19/2203; A61B 2017/2211; A61B 2017/2269; A61M 25/0136
See application file for complete search history.

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2005087128 A1 | 9/2005 |
| WO | 2007008967 A2 | 1/2007 |
| WO | 2009092059 A2 | 7/2009 |

OTHER PUBLICATIONS

WIPO, International Preliminary Report on Patentability; PCT/US2006/027024; Jan. 16, 2008; 8pgs.
(Continued)

*Primary Examiner* — Julie A Szpira
(74) *Attorney, Agent, or Firm* — The Marbury Law Group, PLLC

(57) ABSTRACT

Various embodiments provide systems and methods for controlling a catheter with a catheter positioning device by using a remote controller. As the catheter is advanced by the catheter positioning device, a counterweight may be adjusted to balance the catheter positioning system. In further embodiments, the counterweight may be configured to move to balance a sled member such that any total moment exerted on a sled base remains constant. In further embodiments, the counterweight may be controlled by a control system based on one or more sensors coupled with the catheter positioning system.

9 Claims, 12 Drawing Sheets

(52) U.S. Cl.
CPC ... *A61B 2090/064* (2016.02); *A61B 2090/067* (2016.02); *A61B 2090/504* (2016.02); *A61B 2090/5025* (2016.02); *A61M 2205/332* (2013.01); *A61M 2205/3331* (2013.01)

(56) References Cited

U.S. PATENT DOCUMENTS

| | | | |
|---|---|---|---|
| 5,226,892 A | 7/1993 | Boswell | |
| 5,644,551 A | 7/1997 | Carmichael et al. | |
| 5,649,956 A | 7/1997 | Jensen et al. | |
| 5,682,890 A | 11/1997 | Kormos et al. | |
| 5,810,880 A | 9/1998 | Jensen et al. | |
| 5,814,038 A | 9/1998 | Jensen et al. | |
| 5,827,313 A * | 10/1998 | Ream | A61B 5/0066 600/471 |
| 5,855,583 A | 1/1999 | Wang et al. | |
| 6,007,550 A | 12/1999 | Wang et al. | |
| 6,063,095 A | 5/2000 | Wang et al. | |
| 6,080,181 A | 6/2000 | Jensen et al. | |
| 6,096,004 A | 8/2000 | Meglan et al. | |
| 6,132,368 A | 10/2000 | Cooper | |
| 6,171,234 B1 | 1/2001 | White et al. | |
| 6,171,277 B1 | 1/2001 | Ponzi | |
| 6,200,315 B1 | 3/2001 | Gaiser et al. | |
| 6,346,072 B1 | 2/2002 | Cooper | |
| 6,396,232 B2 | 5/2002 | Haanpaa et al. | |
| 6,398,755 B1 | 6/2002 | Belef et al. | |
| 6,413,264 B1 | 7/2002 | Jensen et al. | |
| 6,445,984 B1 | 9/2002 | Kellogg | |
| 6,461,372 B1 | 10/2002 | Jensen et al. | |
| 6,527,782 B2 | 3/2003 | Hogg et al. | |
| 6,620,174 B2 | 9/2003 | Jensen et al. | |
| 6,726,675 B1 | 4/2004 | Beyar | |
| 6,788,999 B2 | 9/2004 | Green | |
| 6,850,817 B1 | 2/2005 | Green | |
| 6,963,792 B1 | 11/2005 | Green | |
| 6,974,465 B2 | 12/2005 | Belef et al. | |
| 6,999,852 B2 | 2/2006 | Green | |
| 7,006,895 B2 | 2/2006 | Green | |
| 7,090,683 B2 | 8/2006 | Brock et al. | |
| 7,118,582 B1 | 10/2006 | Wang et al. | |
| 7,169,141 B2 | 1/2007 | Brock et al. | |
| 7,204,844 B2 | 4/2007 | Jensen et al. | |
| 7,214,230 B2 | 5/2007 | Brock et al. | |
| 7,276,044 B2 | 10/2007 | Ferry et al. | |
| 7,314,230 B2 | 1/2008 | Kumagai et al. | |
| 7,331,967 B2 | 2/2008 | Lee et al. | |
| 7,357,774 B2 | 4/2008 | Cooper | |
| 7,371,210 B2 | 5/2008 | Brock et al. | |
| 7,377,906 B2 * | 5/2008 | Selkee | A61M 25/0147 604/528 |
| 7,537,570 B2 | 5/2009 | Kastelein | |
| 7,630,752 B2 | 12/2009 | Viswanathan | |
| 7,648,513 B2 | 1/2010 | Green et al. | |
| 7,758,564 B2 * | 7/2010 | Long | A61B 1/00133 600/118 |
| 8,046,049 B2 | 10/2011 | Govari et al. | |
| 8,480,618 B2 * | 7/2013 | Wenderow | A61M 25/0113 604/95.01 |
| 8,672,880 B2 | 3/2014 | Cohen et al. | |
| 2001/0053879 A1 | 12/2001 | Mills et al. | |
| 2002/0042620 A1 | 4/2002 | Julian et al. | |
| 2002/0072704 A1 | 6/2002 | Mansouri-Ruiz | |
| 2002/0120254 A1 | 8/2002 | Julian et al. | |
| 2002/0177789 A1 | 11/2002 | Ferry et al. | |
| 2002/0183723 A1 | 12/2002 | Belef et al. | |
| 2004/0077942 A1 | 4/2004 | Hall et al. | |
| 2004/0254566 A1 * | 12/2004 | Plicchi | A61B 34/37 606/1 |
| 2005/0038412 A1 | 2/2005 | Rabiner et al. | |
| 2005/0065435 A1 | 3/2005 | Rauch et al. | |
| 2005/0113719 A1 | 5/2005 | Saadat | |
| 2005/0203382 A1 | 9/2005 | Govari et al. | |
| 2005/0209614 A1 * | 9/2005 | Fenter | A61B 17/11 606/153 |
| 2005/0222554 A1 | 10/2005 | Wallace et al. | |
| 2005/0228440 A1 * | 10/2005 | Brock | A61B 34/71 606/205 |
| 2005/0277874 A1 | 12/2005 | Selkee | |
| 2005/0283140 A1 | 12/2005 | Jensen et al. | |
| 2006/0009735 A1 | 1/2006 | Viswanathan et al. | |
| 2006/0041181 A1 | 2/2006 | Viswanathan et al. | |
| 2006/0084911 A1 | 4/2006 | Belef et al. | |
| 2006/0084945 A1 | 4/2006 | Moll et al. | |
| 2006/0095022 A1 | 5/2006 | Moll et al. | |
| 2006/0161136 A1 | 7/2006 | Anderson et al. | |
| 2006/0161137 A1 | 7/2006 | Orban et al. | |
| 2006/0161138 A1 | 7/2006 | Orban et al. | |
| 2006/0167441 A1 | 7/2006 | Wang et al. | |
| 2006/0178559 A1 | 8/2006 | Kumar et al. | |
| 2006/0229587 A1 | 10/2006 | Beyar | |
| 2006/0235436 A1 | 10/2006 | Anderson et al. | |
| 2006/0270915 A1 | 11/2006 | Ritter et al. | |
| 2006/0293643 A1 | 12/2006 | Wallace et al. | |
| 2007/0012135 A1 | 1/2007 | Tierney et al. | |
| 2007/0016174 A1 | 1/2007 | Millman et al. | |
| 2007/0019330 A1 | 1/2007 | Wolfersberger | |
| 2007/0021776 A1 | 1/2007 | Jensen et al. | |
| 2007/0043338 A1 | 2/2007 | Moll et al. | |
| 2007/0043455 A1 | 2/2007 | Viswanathan et al. | |
| 2007/0149946 A1 | 6/2007 | Viswanathan et al. | |
| 2007/0233044 A1 | 10/2007 | Wallace et al. | |
| 2007/0239172 A1 | 10/2007 | Lee et al. | |
| 2007/0250073 A1 | 10/2007 | Brock et al. | |
| 2007/0250074 A1 | 10/2007 | Brock et al. | |
| 2007/0260115 A1 | 11/2007 | Brock et al. | |
| 2007/0276423 A1 | 11/2007 | Green | |
| 2007/0283263 A1 | 12/2007 | Zawde et al. | |
| 2007/0299479 A1 | 12/2007 | Saksena | |
| 2008/0009791 A1 | 1/2008 | Cohen et al. | |
| 2008/0039869 A1 | 2/2008 | Mills et al. | |
| 2008/0045892 A1 | 2/2008 | Ferry et al. | |
| 2008/0059598 A1 | 3/2008 | Garibaldi et al. | |
| 2008/0119824 A1 | 5/2008 | Weitzner et al. | |
| 2008/0119872 A1 | 5/2008 | Brock et al. | |
| 2008/0125793 A1 | 5/2008 | Brock et al. | |
| 2008/0125794 A1 | 5/2008 | Brock et al. | |
| 2008/0140087 A1 | 6/2008 | Barbagli | |
| 2008/0147091 A1 | 6/2008 | Cooper | |
| 2008/0183136 A1 | 7/2008 | Lenker et al. | |
| 2008/0215065 A1 | 9/2008 | Wang et al. | |
| 2008/0245946 A1 | 10/2008 | Yu | |
| 2008/0249536 A1 | 10/2008 | Stahler et al. | |
| 2008/0300592 A1 | 12/2008 | Weitzner et al. | |
| 2009/0012533 A1 | 1/2009 | Barbagli et al. | |
| 2009/0082722 A1 | 3/2009 | Munger et al. | |
| 2009/0105639 A1 | 4/2009 | Weitzner et al. | |
| 2009/0105645 A1 | 4/2009 | Kidd et al. | |
| 2009/0248043 A1 | 10/2009 | Tierney et al. | |
| 2010/0010475 A1 | 1/2010 | Teirstein et al. | |
| 2010/0256558 A1 | 10/2010 | Olson et al. | |
| 2011/0077590 A1 | 3/2011 | Plicchi et al. | |
| 2012/0182134 A1 | 7/2012 | Doyle | |
| 2012/0184955 A1 | 7/2012 | Pivotto et al. | |
| 2012/0197182 A1 | 8/2012 | Millman et al. | |
| 2012/0220931 A1 * | 8/2012 | Cohen | A61M 25/0105 604/95.01 |
| 2013/0138118 A1 | 5/2013 | Doyle | |
| 2013/0317519 A1 * | 11/2013 | Romo | A61B 34/30 606/130 |

OTHER PUBLICATIONS

State Intellectual Property Office of the People's Republic of China, First Office Action, Oct. 30, 2009, Chinese Patent Application 200680025512.7, "Remotely Controlled Catheter Insertion System," with English translation, (24 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

(56) References Cited

OTHER PUBLICATIONS

International Preliminary Report on Patentability, Intl Application PCT/US2009/031357. International Bureau of WIPO, Jul. 29, 2010.
International Search Report and Written Opinion, Intl Application PCT/US2009/031357. International Search Authority, U.S. Patent and Trademark Office (ISA/US), Mar. 19, 2009.
U.S. Appl. No. 13/051,736, Final Office Action dated Nov. 5, 2012.
Hein et al., "Robot Supported Insertion of Catheters for Hyperthermia and Branch Therapy," Computer Assisted Radiology and Surgery, 1998, pp. 660-663.
Macoviak, "Catheter System for Surgical Access and Circulatory Support of the Heart," USPTO, Official Gazette, vol. 1278, Jan. 6, 2004.
U.S. Appl. No. 13/051,736, Non-Final Office Action dated Jul. 17, 2012.
U.S. Appl. No. 12/903,397, Non-Final Office Action dated Nov. 19, 2012.
Canadian Application 2,646,846, Office Action dated Sep. 19, 2012.
Extended European Search Report of Apr. 17, 2013; European Application No. 09702983.9.
Japanese Patent Application No. 2010-543298; Office Action of Mar. 19, 2013.
U.S. Appl. No. 13/461,463, Final Office Action dated Jun. 27, 2014.
U.S. Appl. No. 13/461,463, Non-Final Office Action dated Oct. 31, 2014.
U.S. Appl. No. 12/515,005, Non-Final Office Action dated Apr. 11. 2013.
U.S. Appl. No. 13/078,663, Non-Final Office Action dated Aug. 14, 2014.

\* cited by examiner

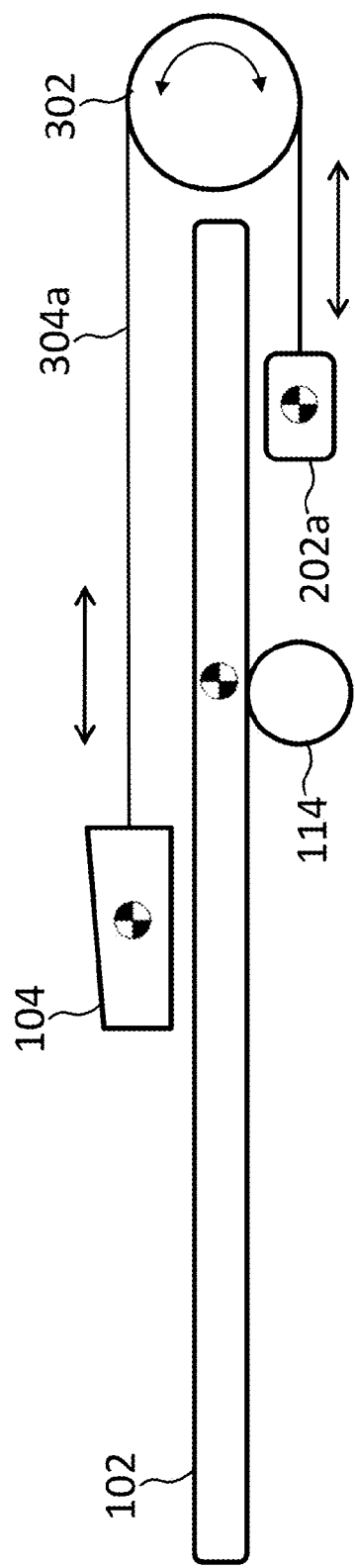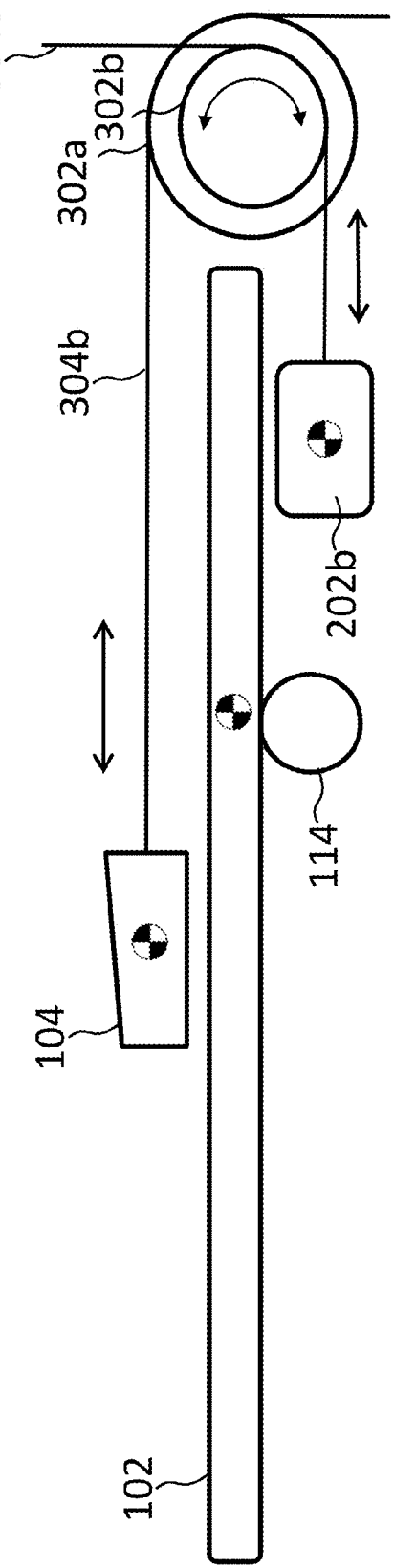

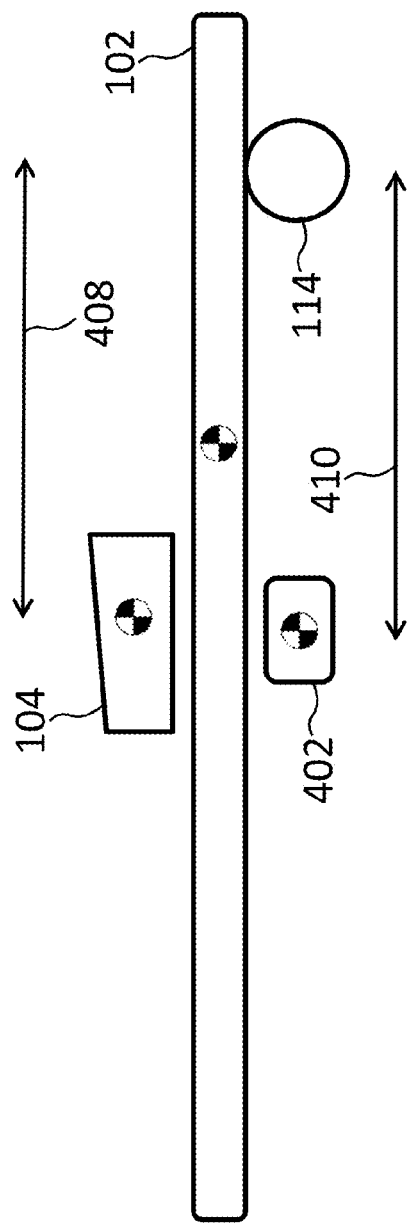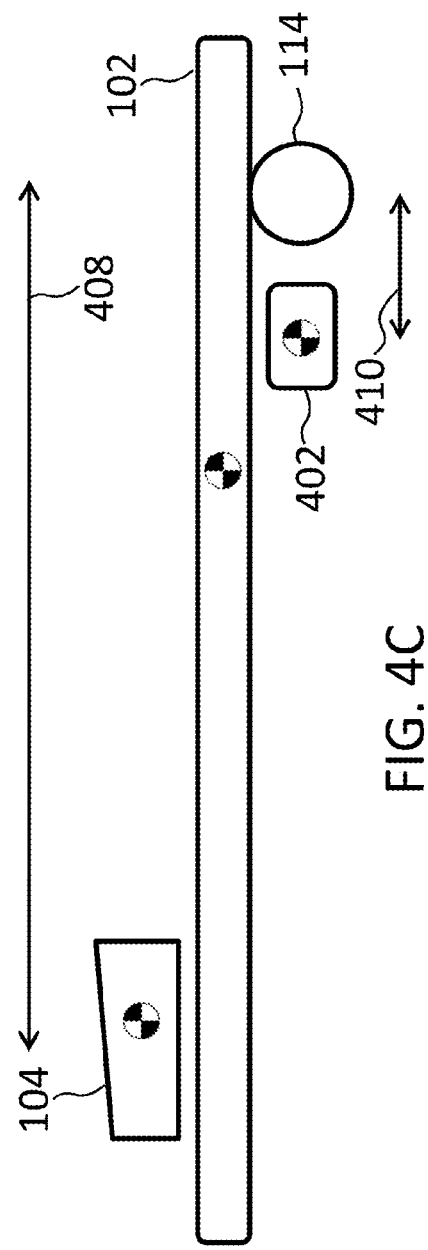

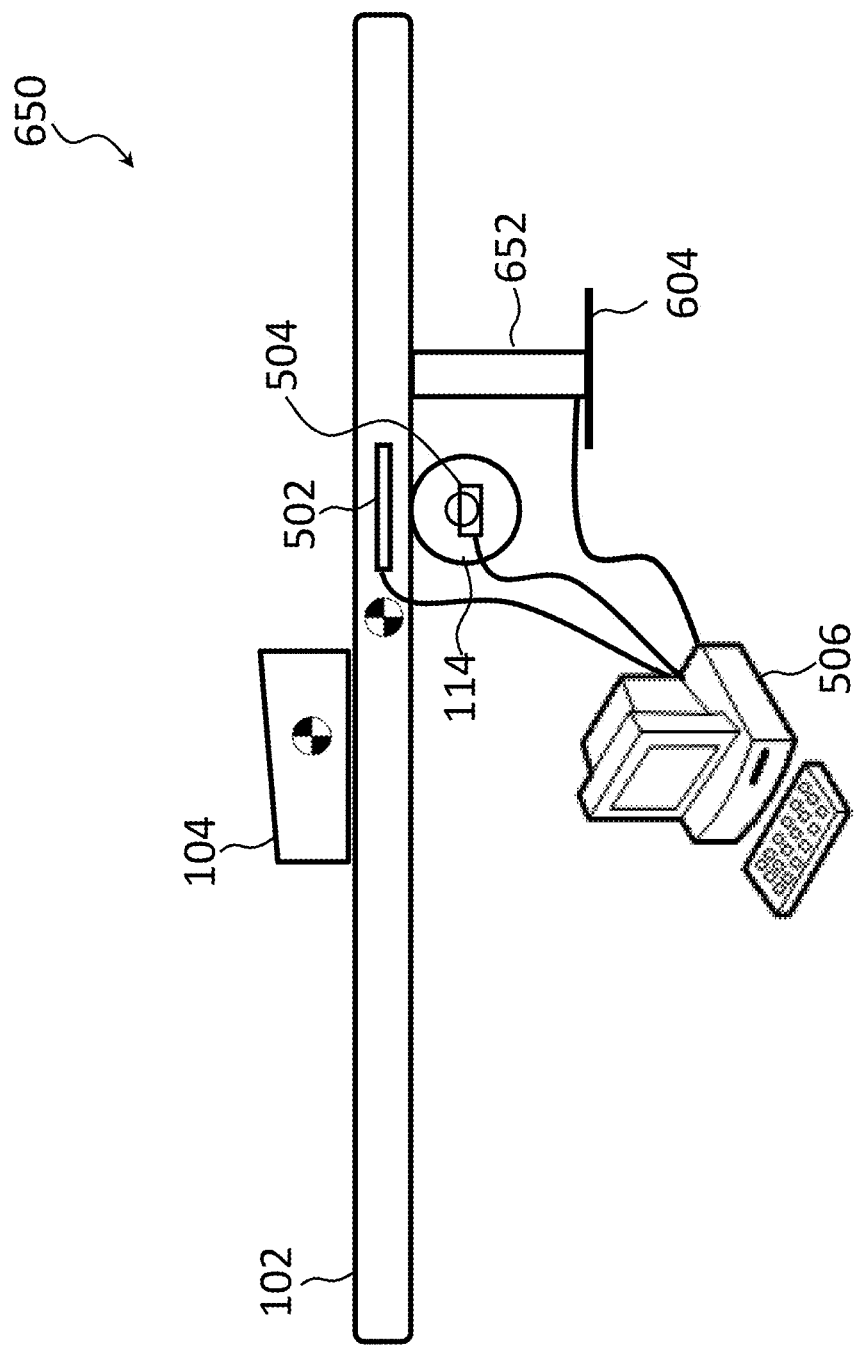

COMPONENTS AND METHODS FOR BALANCING A CATHETER CONTROLLER SYSTEM WITH A COUNTERWEIGHT

CROSS-REFERENCE TO RELATED APPLICATIONS

The present invention claims the benefit of priority to U.S. Provisional Patent Application No. 61/870,311, entitled "COMPONENTS AND METHODS FOR BALANCING A CATHETER CONTROLLER SYSTEM WITH A COUNTERWEIGHT," filed Aug. 27, 2013, the entire contents of which are incorporated herein by reference.

BACKGROUND

Many invasive medical procedures require the use of radiation to visualize and track the location of an inserted device. For example, procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system.

High dosages of radiation may have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury or degradation.

SUMMARY OF THE INVENTION

The various embodiments include a catheter positioning system having a sled member configured to accept a handle of a catheter and a sled base configured to move the sled member along a length of the sled base in order to position the catheter within a patient, that also features a counterweight moveably coupled to the sled base by a drive mechanism that is configured to move the counterweight in order to reduce shifting of the center of mass of the sled member, sled base and counterweight as the sled member is moved along the sled base. In an embodiment, the counterweight is moveably coupled to the sled base and the drive mechanism is configured so that the counterweight moves along the length of the sled base. In an embodiment, the drive mechanism includes a cable coupled between the counterweight and the sled member and passing around at least one pulley that is configured so that the counterweight moves in a direction opposite to that of the sled member. In an embodiment in which the counterweight has a weight substantially similar to that of the sled member the drive mechanism may be configured so that the counterweight moves the same distance as the sled member, though in the opposite direction. If the counterweight has a weight substantially different from that of the sled member, the drive mechanism may be configured so that the counterweight moves a distance that is approximately equal to the distance moved by the sled member times the ratio of the weight of the sled member divided by the weight of the counterweight.

In an embodiment, the drive mechanism may include a drive motor and at least one gear coupled to the drive motor.

In a further embodiment, the catheter positioning system may include a sensor coupled to the catheter positioning system, and a control system coupled to the sensor that is configured to control the drive mechanism to move the counterweight based on data from the sensor. In this embodiment, the sensor may be any one or more of a tilt sensor, a pressure sensor, a stress sensor, and a strain sensor. Overall, the counterweight may be configured on the catheter positioning system to move in response to movements of the sled member so that a bending moment applied to a support structure supporting the sled base remains approximately constant.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIG. 3A is a system diagram illustrating an embodiment system with a sled member coupled to a counterweight by a pulley.

FIG. 3B is a system diagram illustrating an embodiment system with a sled member coupled to a counterweight by pulleys of different sizes.

FIGS. 4A-4C are diagrams illustrating a sequence of relative motions of a sled member and a counterweight in an embodiment catheter positioning system.

FIG. 6B is a system diagram of an embodiment system with an active damping system controlled by a control system based on sensor inputs.

DETAILED DESCRIPTION

Figure 1:
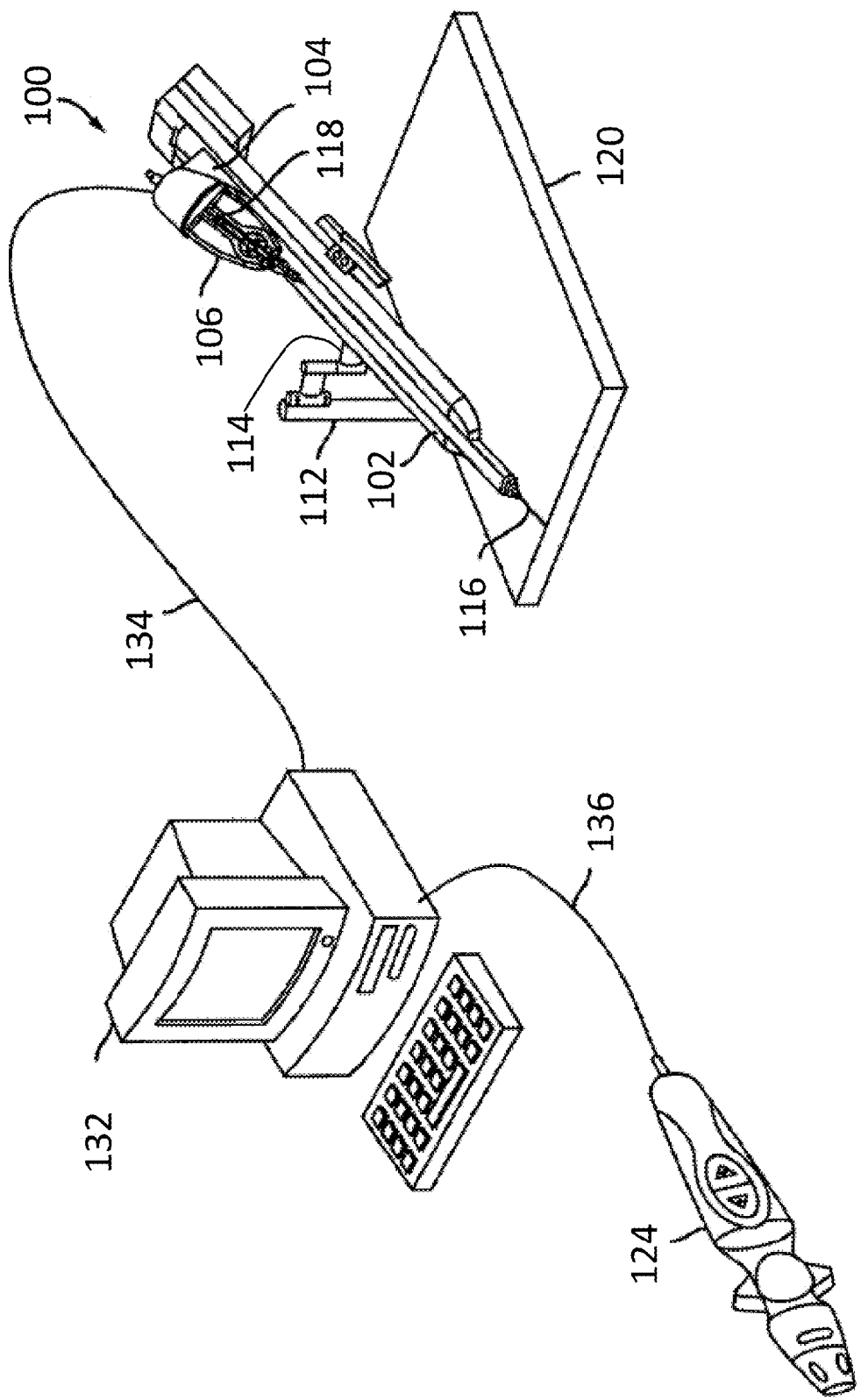
FIG. 1 is a system diagram illustrating a remote controller, a remotely controlled catheter system, and a programmable control system.

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

Various embodiments provide systems and methods for reducing bending moments in a catheter positioning system during catheterization procedures. The embodiment systems allow a physician to remotely control a catheter position within a patient while being positioned away from sources of radiation used for imaging, thereby avoiding harm associated with repeated exposure to radiation or caused by heavy protective gear. A catheter positioning device provides a telerobotic capability to advance and rotate an attached catheter within a patient's body. The catheter positioning device may also be used to actuate the catheter, such as by controlling an actuator on a catheter's handle to deflect a tip to help in navigation. An example of a catheter positioning device is disclosed in PCT Application PCT/US2009/0311357, which published as WO 1009/092059 and is incorporated herein by reference in its entirety for details of the catheter positioning device.

A catheter positioning system such as disclosed in WO 1009/092059 functions to advance or withdraw the catheter longitudinally in order to advance or withdraw the catheter within the patient's body. Since the catheter enters the patient's body at a single point, the catheter positioning system may include a rail or sled base along which a sled member holding the catheter handle advances, and a support structure that holds the rail or sled base in a fixed orientation with respect to the patient. For example, the support structure may be a bridge or arm that extends over a table to hold the catheter positioning system rail or sled base at a fixed elevation an angle with respect to the patient.

The sled member may itself include drive motors for rotating the catheter handle, and thus may be heavy. As the sled member advances along the rail or sled base, the distance between the sled member and the support structure holding the rail or sled base will change. As a result, a bending moment applied to the support structure will change as the moment arm (i.e., the distance between the sled member and the support structure) changes. For example, when the catheter is fully withdrawn from the patient and the sled member near a distal end of the rail or sled base, the bending moment applied to the support structure may be significantly greater than when the catheter is partially inserted such that the sled member is positioned near the support structure. Patient safety requires that the angle of insertion of the catheter remain as steady as possible, so the support structure must be sufficiently rigid as to accommodate this change in bending moment without deflecting during a procedure. However, this requirement may add substantial mass and cost to the support structure, and limit the types of support structures that may be implemented.

In various embodiments the catheter positioning device address the problem of changes in the bending moment applied to a support structure by including a counterweight system configured to maintain a consistent center of mass of the system as a catheter is positioned. In overview, the counterweight may be of sufficient mass and coupled to a drive mechanism that moves the mass in conjunction with movement of the sled member so as to at least partially overcome changes in the bending moment applied to a support structure. By functioning to maintain an approximately consistent center of mass system, embodiment counterweight systems may help to keep the catheter positioning device stable during catheterization procedures, while reducing the strength and weight of the device support structures.

In an embodiment, the counterweight may be moved by various mechanical mechanisms, such as a pulley system or gear drive, in response to the motion of the sled member of the catheter positioning system. In further embodiments, a control system may control movement of the counterweight based on one or more sensors for detecting the position of the sled member along the rail or sled base, bending stress applied to the support structure, and/or strain in various parts of the catheter positioning device or support structure.

FIG. 1 illustrates an embodiment catheter positioning device 100 with a remote controller 124. The catheter positioning device 100 may include a sled base 102 coupled with a sled member 104. The sled base 102 may be configured to advance the sled member 104 along the sled base 102 towards the body of the patient or back away from the patient. For example, the sled member may be moved with a motor at one end of the sled base 102. The sled member 104 may be driven along a rail or sled base 102 by a drive mechanism, such as a worm drive, in order to advance or withdraw the catheter.

The sled base may be held in position above a patient or operating table 120 by a bridge (not shown) or support arm 112 that includes a sled base support structure 114 that holds the sled base 102 in a fixed position and orientation. The arm 112 may be extended or rotated to position the sled base 102 relative to a patient on the operating table 120. The sled base may also include a nose cone 116 that supports insertion of the catheter into a patient. A catheter may be advanced along the sled base 102 by the sled member 104 so that it passes through the nose cone 116 and into the patient.

The sled base 102 may include a sterile barrier configured to support and protect the catheter. The sterile barrier may include a resealable delivery channel configured to receive and guide the catheter along the sled base as it is advanced by the sled member 104. For example, the catheter may be inserted into the delivery channel and then the catheter handle 118 may be connected to the sled member 104 (such as by using the modular plate 106 discussed below) such that the catheter is driven forward by translation of the sled member 104 along the resealable delivery channel in the sled base 102 and through the nose cone 116 into the patient.

The sled member 104 may be coupled to a modular plate 106 to which a catheter handle 118 may be attached. Many alternate modular plates 106 that may be swapped out so that the catheter positioning system may be used with many different types of catheters. Depending on the kind of catheter that is desired for a procedure, an appropriate modular plate 106 may be attached to the sled member 104 and the catheter may be attached to the module plate 106. The modular plate 106 may also integrate with any actuators on the catheter handle 118 thereby allowing an operator to control the actuators via the remote controller 124.

The sled member 104 may be rotated by a drive mechanism in order to rotate a catheter connected to the modular plate 106. This rotation may be controlled remotely via the remote controller 124. By controlling translation along the sled base 102, rotation of the sled member 104, and actuation of the catheter's handle via the modular plate 106, an operator may position or use the catheter in any way necessary for a desired operation. Further, an operator may control each of these degrees of freedom (i.e., translation, rotation, and actuation) remotely with the remote controller 124.

A remote controller 124 may be connected to a programmable control system 132 by a wired connector 136 or a wireless data link (not shown). The programmable control system 132 may also be connected to the catheter positioning device 100 by a wired connector 134 or a wireless data link (not shown). The programmable control system 132 may output command signals to the positioning device 100 based on training or programming, such as programmed movements for automatic positioning of the catheter.

Figure 2A:
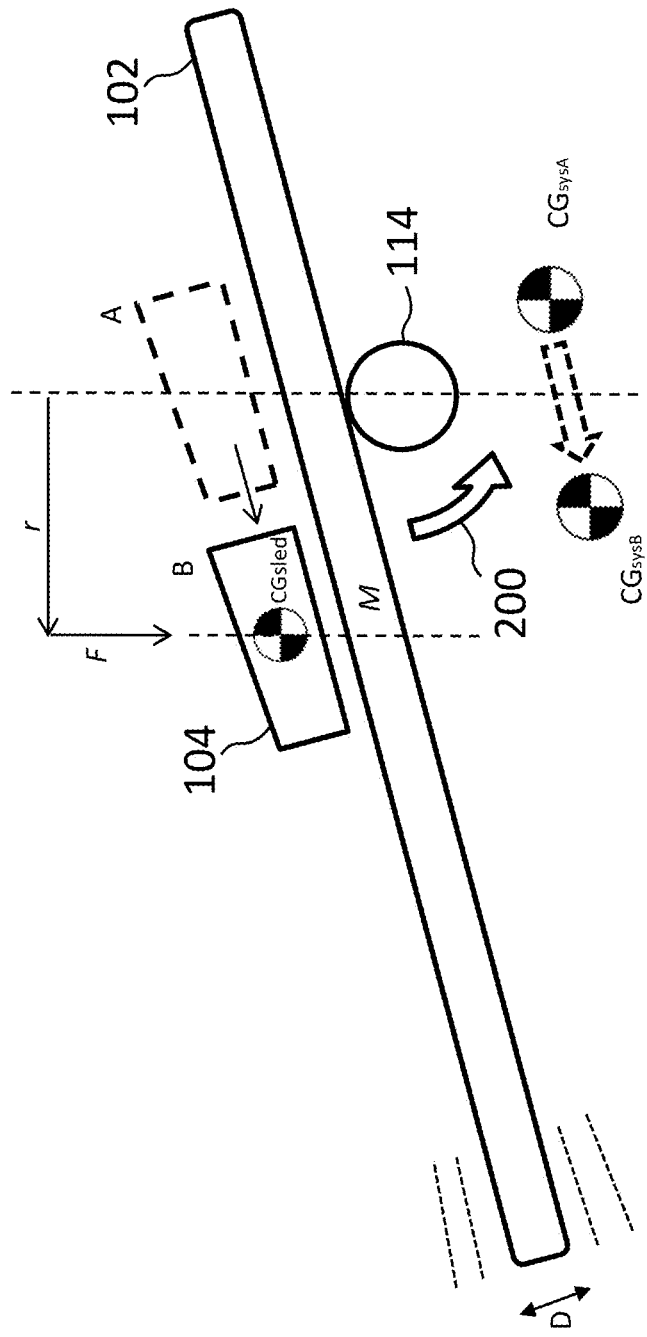
FIG. 2A is a system diagram illustrating a catheter positioning system, a slide member and a bending moment generated by the slide member on a support structure.

FIG. 2A illustrates a catheter positioning device without a counterweight in order to illustrate the problem of the changing bending moment applied to a sled base support structure 114 as the sled member 104 moves along the rail or sled base, such as from position A to position B. As a sled member 104 advances down a sled base 102, the system's center of mass will shift, such as from $CG_{sysA}$ to $CG_{sysB}$, and the sled base 102 will apply a bending moment to the sled base support structure 114, which will apply a torque to a support arm 112, in the direction of the arrow 200 shown in FIG. 2A. Generally, a torque or bending moment "M" equals the vector cross product of a force vector "F" and a distance vector "r" (e.g., M=F×r). For example, the torque or bending moment M is the value or magnitude of a force vector F, in this case the downward force of the weight of the sled member 104, times its moment arm r, which is the distance from the weight (e.g., the center of mass) to the point of analysis, such as approximately the center of the support structure 114. Thus, the further sled member 104 is from the support structure 114, the greater the bending moment applied to the sled base 102 (e.g., and torque applied to the support structure 114). Deflection of the sled base 102 (e.g., deflection D) due to bending moments generated from movement of the sled member 104, may shift the introducer and/or catheter at the point of entry into the patient thereby potentially disrupting an ongoing operation or procedure. Various embodiments avoid these potential problems by using a moveable counterweight to compensate for movement of the sled member 104 on the sled base 102, and to thereby maintain a relatively constant center of mass of the system and reduce or eliminate deflection. The various respective centers of mass throughout the figures of sled members, counter weights, sled base support structures and positioning systems are shown for illustrative purposes only. One of skill in the art will recognize that the placement of the centers may not be to scale and may not accurately represent the actual locations or positions of these centers of mass in an actual system.

Figure 2B:
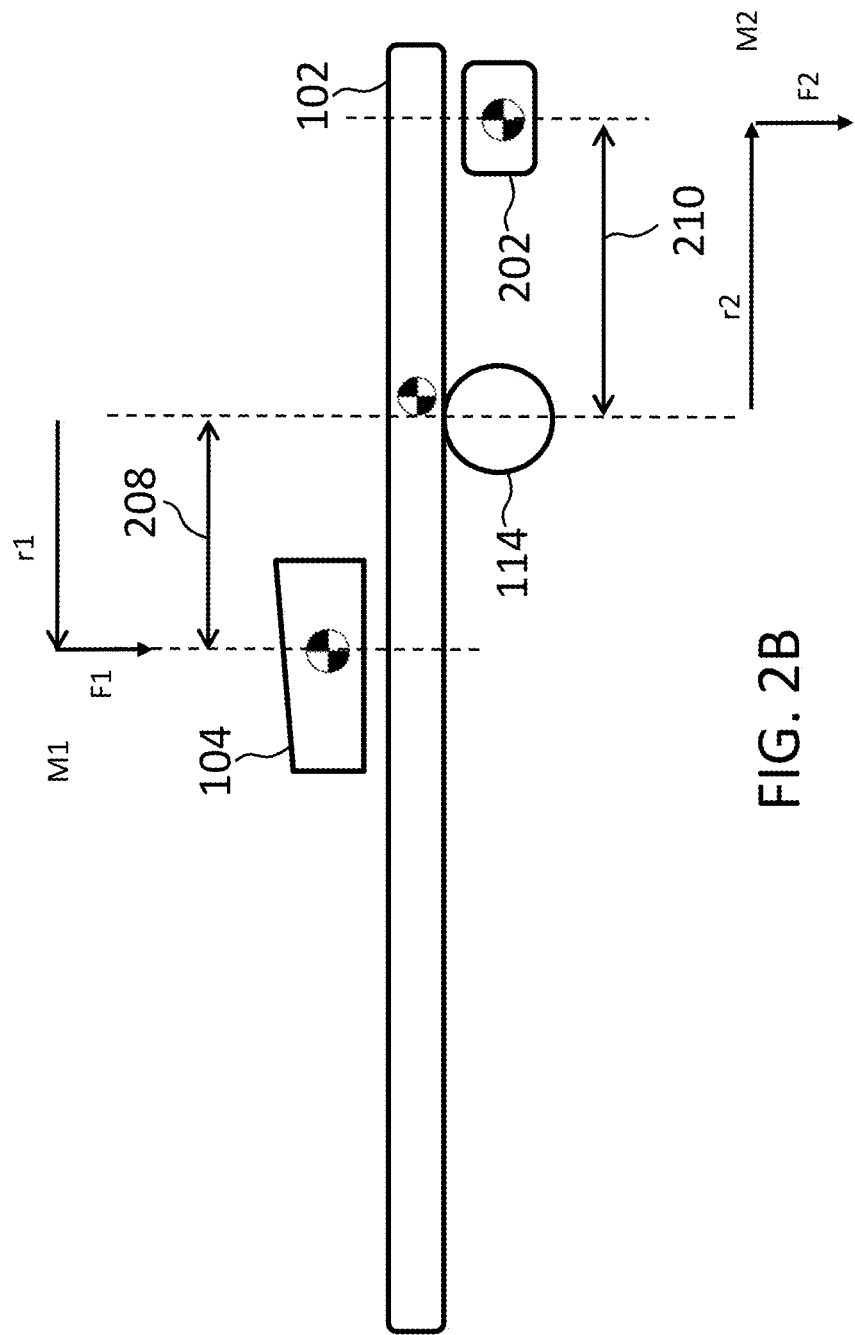
FIG. 2B is a system diagram illustrating an embodiment catheter positioning system with a counterweight

FIG. 2B illustrates an embodiment system with a counterweight 202 coupled to the sled base 102 and configured to counter balance the sled member 104 about the support structure 114. As the sled member 104 moves along the sled base 102 to position the catheter, a bending moment M1 is applied. The counterweight 202 may be moved in the opposite direction in an amount that will apply a compensating bending moment M2. Because of the action of the counterweight 202, the center of mass of the system, including the support structure 114 will remain relatively constant and deflection of the sled base 102 may be reduced or eliminated.

The counterweight 202 creates a bending moment M2, which may be applied as a torque about the support structure 114 that is approximately equal to the bending moment M1. Because the bending moment M2 is applied on the opposite side of the support structure 114, the bending moment M2 applies a force in the opposite direction of the bending moment M1 applied by sled member 104 (e.g., due to the support structure 114 acting as a fulcrum). The moment arm 210 of the counterweight 202 extends from the center of mass of the counterweight 202 to the center of the support structure 114. The moment arm 208 of the sled member 104 extends from the center of mass of the sled member 104 to the center of the support structure 114. Thus, the support structure 114 may translate downward forces applied from the counterweight 202 side of the sled base 102 to an upward force on the sled member 104 side of the sled base 102.

As the sled member 104 advances on the sled base 102 to position the catheter, its moment arm 208 changes. For example, the moment arm 208 may decrease as it approaches a mid-point of the support structure 114. The moment arm 208 may increase as it approaches full travel in a direction away from the support structure 114. Thus, because the force of the sled member 104 (e.g., mass or weight) remains constant, the bending moment M1 applied to the support structure 114 from the sled member 104 changes in direct proportion to the length of the moment arm 208, such as r1.

To counter this change in the bending moment M1 applied due to the sled member 104 and to help prevent deflection and tilting of the sled base 102, a bending moment M2 may be exerted by the counterweight 202 that counters the bending moment M1. As the position of the sled base 102 changes, the position of the counterweight 202 may be changed in the opposite direction by moving the counterweight 202 towards or away from the support structure 114 to increase or decrease its moment arm 210. If the counterweight 202 and sled member 104 are on opposite sides of the support structure 114, the moments may act about the same axis (i.e., the support structure 114) but in opposite directions with the support structure 114 acting as a fulcrum (e.g., similar to children balancing on a seesaw).

In embodiments in which the sled member 104 and counterweight 202 weigh the same, then the counterweight 202 may be moved a distance equal to the distance of travel of the sled member 104 (though in an opposite direction). In other embodiments, the mass of the counterweight 202 may be different from that of the sled member 104. In such embodiments, the amount of travel of the counterweight 202 may be equal to the distance of travel of the sled member times the ratio of the masses of the sled member to the counterweight. Again, this is because bending moment is equal to the weight times the moment arm. In examples, such as when the support structure is located toward one end of the sled base 102, an insufficient amount of distance on the counterweight 202 side of the sled base 102 may exist between the end of the sled base 102 and the support structure 114. Limiting the range of movement of the counterweight 202. Thus, the limited range of movement of the counterweight 202 may be compensated for by increasing its mass compared to the sled member 104. Thus, a relatively shorter moment arm 210 may nevertheless produce a sufficient bending moment M2 to compensate for the bending moment M2 when the mass of the counterweight 202 is increased.

In the various embodiments, any of a number of drive mechanisms may be used to move the counterweight 202 in response to movements of the sled member 104

Figure 2C:
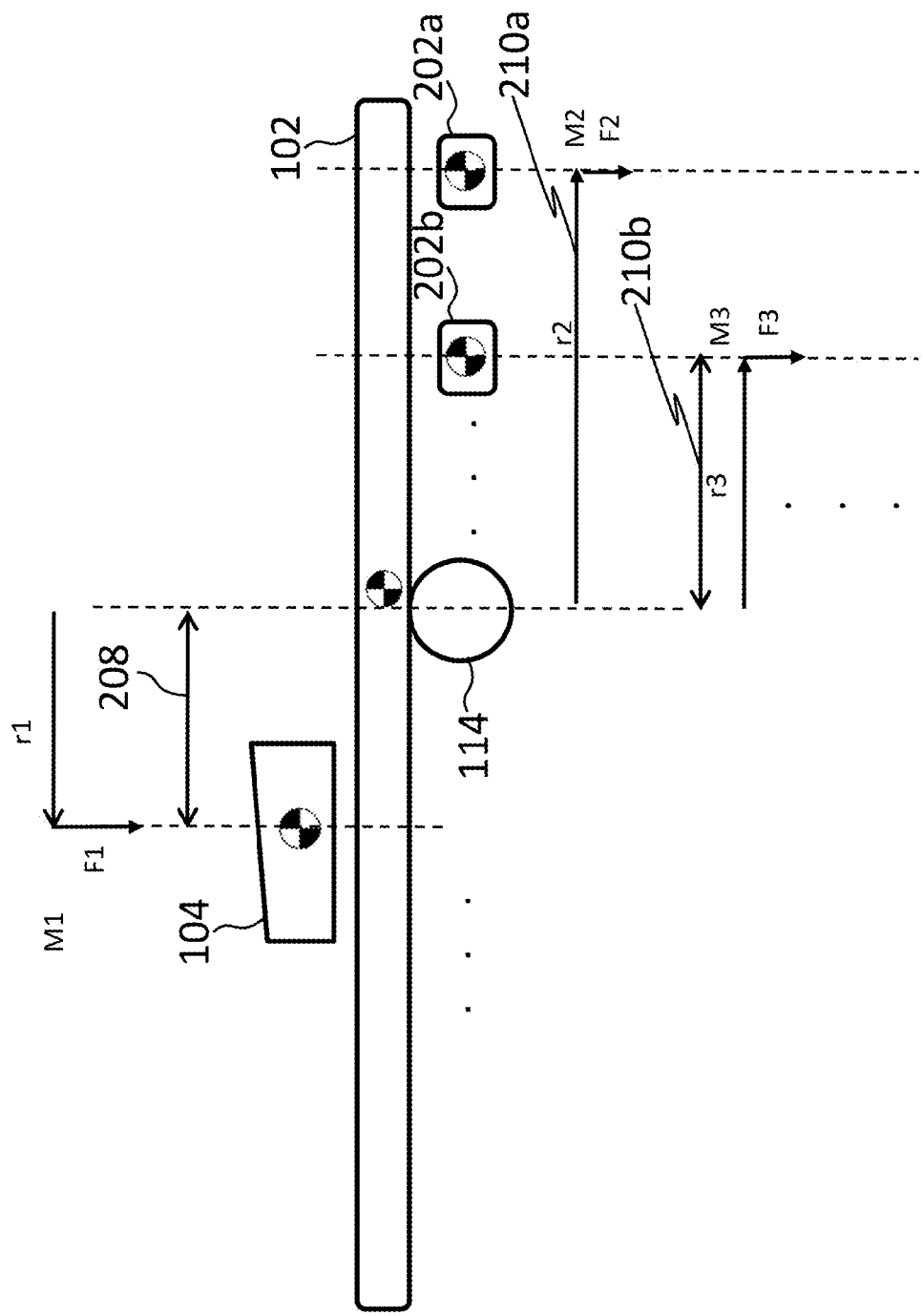
FIG. 2C is a system diagram illustrating an embodiment catheter positioning system with a series of counterweights.

In further embodiments, as illustrated in FIG. 2C, a series of counterweights (e.g., 202a, 202b, . . . ) may be used to provide a balancing for the movement of the sled member 104 on the sled base 102. For example, a first counterweight 202a may be positioned at a distance r2 210a from the support structure 114 and a second counterweight 202b may be positioned at a distance r3 210b from the support structure 114. In some embodiments, the first and second counterweights 202a and 202b may be smaller than the counterweight 202 illustrated in FIGS. 2A and 2B. Also, additional counterweights may be used on either side of the support structure 114. The first counterweight 202a may produce a first moment M2 that is the cross product of the force vector F2 and the distance r2. The second counterweight 202b may produce a second moment M3 that is the cross product of the force vector F3 and the distance r3. The positions of the first and second counterweights 202a and 202b may be controlled individually to provide fine control over the counterbalancing action. For example, when acceleration components are present in the movement of the sled member 104, the use of additional counterweights may provide a greater degree of control over the movement of the first and second counterweights 202a and 202b or additional counterweights to compensate for complex bending forces.

Figure 2D:
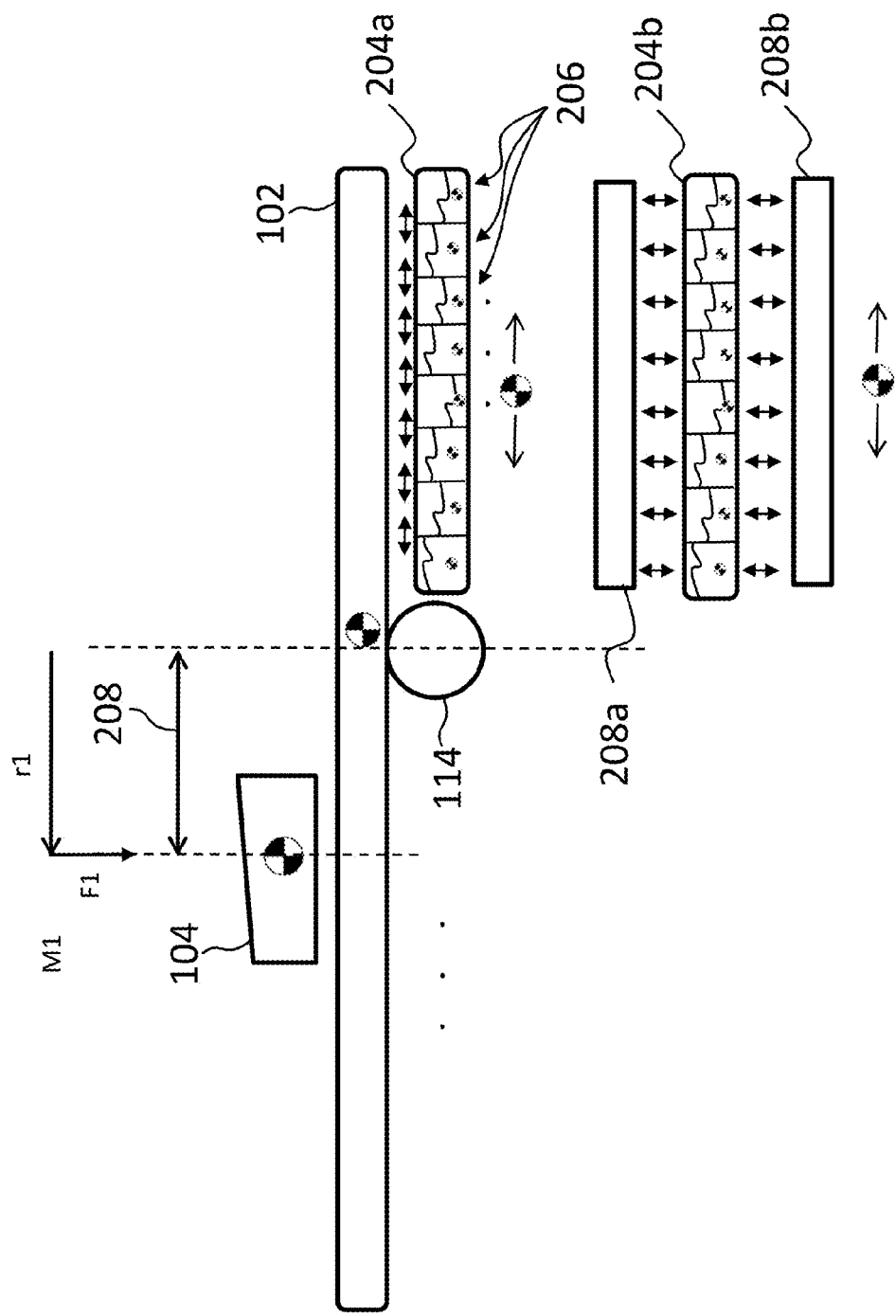
FIG. 2D is a system diagram illustrating an embodiment catheter positioning system with a distributed liquid counterweight.

In a further embodiment illustrated in FIG. 2D, a liquid counterbalancing mechanism 204 may be used to provide counterbalancing. In a liquid counterbalancing mechanism 204a, a series of chambers 206 may contain a liquid, such as water, oil, or mercury. The counterbalancing mechanism 204a may be configured such that the liquid is pumped back and forth between the chambers 206, either passively or actively, in order to provide a compensating counterweight. In a passive embodiment, such as the liquid counterbalancing mechanism 204a illustrated in FIG. 2D, the liquid may be flow between the chambers 206 as the sled member 104 moves on the sled base 102. In active embodiments, liquid may be pumped between the chambers 206, or to and from an external reservoir (not shown) using control mechanisms 208a and 208b (e.g., pumps or a gravity feed system) to provide an active counterbalancing system 204b, the levels of the liquid in the chambers 206 may be controlled. In such embodiments, the movement of the liquid into and out of the various chambers 206 may function to shift the center of gravity of the system similar to movement of counterweights as described herein. Using such a liquid counterbalance mechanism may also serve to dampen some vibrations or jitter in the system due to viscosity effects.

FIG. 3A illustrates an embodiment in which the counterweight 202a is linked with the sled member 104 by a cable 304 about a pulley 302. The cable 304a may thereby directly link the movement of the sled member 104 to the movement of the counterweight 202a. The configuration of the cable 304a and the pulley 302 may also translate the directional movement of the counterweight 202a relative to the sled member 104, such that when the sled member 104 moves in one direction on a first side of the sled base 102, the counterweight 202 moves in an opposite direction on a second side of the sled base 102. In this embodiment, as the sled member 104 moves along the sled base 102, the sled member 104 (or a drive mechanism coupled to the sled member 104) may cause the cable 304a to be taken in or let out. The cable 104 may be guided or redirected by one or more pulleys 302 or cable guides (not shown). The cable 304a may be attached to the counterweight 202a. In this configuration, movement of the sled member 104 will result in a corresponding proportional movement of the counterweight 202a. By the movement of the cable 304a, changes in the moment arm of the sled member 104 may be balanced by changes in the moment arm of the counterweight 202 such that the overall center of mass does not change significantly. In embodiments in which the cable 304 is directly coupled to the sled member 104 on one end, and coupled to the counterweight 202a on the other end through a single pulley 302, displacements in movement may be directly proportional. Thus, such embodiments may be implemented with a counterweight 202a having approximately the same mass as the sled member 104. In this manner, the counterbalancing movement of the counterweight 202 may produce proportional forces (e.g., M2) to counteract changes in the bending moment M1 applied to the support structure 114 by the sled 104 during a catheter positioning procedure.

In another embodiment illustrated in FIG. 3B, one or more additional pulleys 302, such as spools or pulleys 302a and 302b of different sizes, may be arranged on a common axis and may be coupled to respective cables 304b and 304c. The common axis may cause rotation of both of the spools or pulleys 302a and 302b together. By using different sized spools or pulleys 302a and 302b, a translating drive effect may be achieved between the movement of one pulley, and the movement of a different sized spool or pulley. Such translating drive effect may provide a ratiometric relationship between the movement of the sled member 104 and the movement of the counterweight 202b, which may be of a different (e.g., larger) mass than the sled member 104. For example, the ratiometric relationship may be based on the ratios of the respective diameters of the spools or pulleys. In an example in which the counterweight 202b is of a greater mass than the sled member 104, the sled member 104 may be coupled to the larger spool or pulley 302a and the counterweight 202b may be coupled to the smaller spool or pulley 302b. The cables 304b and 304c may be individually controlled.

In a further embodiment, a cable linkage between the sled member 104 and counterweight 202 may include a block and tackle arrangement to enable use of a counterweight that is different from the weight of the sled member. For example, instead of a direct linkage, the counterweight 202 may be coupled to a pulley and the cable fixed to the sled base after passing through the pulley. In this configuration the counterweight will move half as far as the sled member 104 in either direction, so the counterweight may weigh twice as much as the sled member 104.

In further embodiments, the counterweight may be coupled with a retrieval mechanism configured to move the counterweight in the opposite direction. For example, as the sled member 104 moves backwards, a retrieval mechanism may move the counterweight 202 in the opposite direction and draw up any slack in the cable 304. Various retrieval mechanisms may be used, such as a second cable and pulley connected to a motor or the front of the sled member.

Figure 3C:
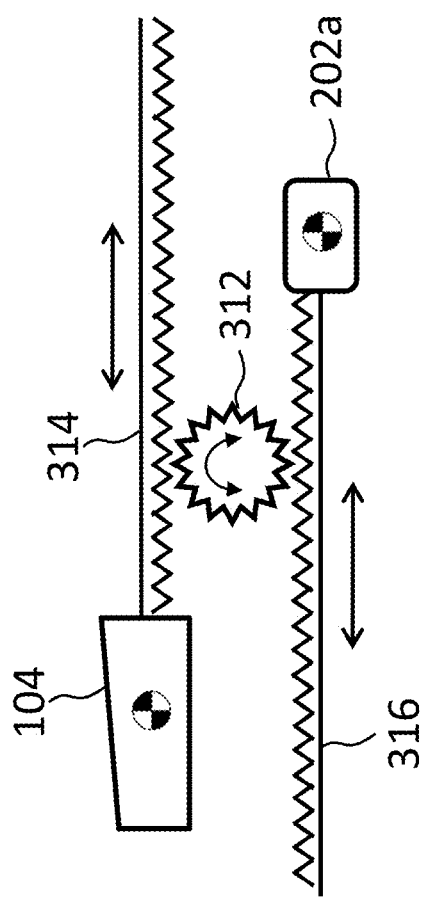
FIG. 3C is a system diagram illustrating an embodiment system with a sled member coupled to a counterweight by a gear.

FIG. 3C illustrates an alternate embodiment for moving the counterweight 202a in response to movements of the sled member 104. In this embodiment, the sled member 104 may be attached to a first toothed arm 314 that is advanced or retracted by a drive gear 312. Similarly, the counterweight 202a may be attached to a second toothed arm 316 that engages the same or a different drive gear 312. If the first arm 314 and second arm 316 are coupled to the same drive gear 312, such that as the sled member 104 advances, the first arm 314 turns the gear 312 that moves the second arm 316 and counterweight 202 an equal distance but opposite in the opposite direction. In this configuration, the counterweight 202 may weigh the same as the sled member 104.

Figure 3D:
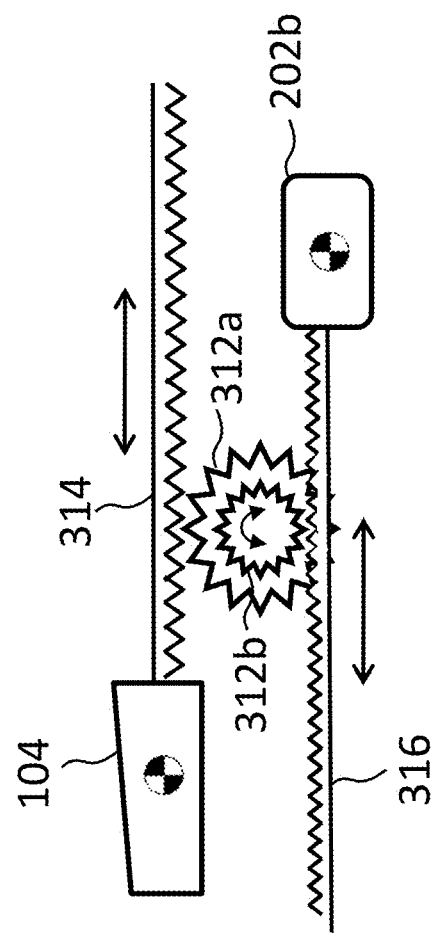
FIG. 3D is a system diagram illustrating an embodiment system with a sled member coupled to a counterweight by gears of different sizes.

In a further embodiment, the counterweight 202b and sled member 104 may have different weights, as illustrated in FIG. 3D. A first gear 312a may be coupled to the arm 314 and the sled member 104. A second gear 312b, having a different tooth size (e.g., smaller) may be coupled to the arm 316 and the counterweight 202b. The gear 312a and 312b may be coupled to a common axis so that each gear rotates together with the other through a common drive. The arm 316 may be configured to move the counterweight 202b a different distance than the sled member 104 due to the ratiometric relationship between the gears 312a and 312b. In various embodiments, the gears 312a and 312b may have a different ratio or number of teeth. For example, if the counterweight 202*b* has a greater mass than the sled member 104, that counterweight may be driven by a coaxial gear 312*b* that has a smaller radius so that the coaxial gear 312*b* drives the second arm 316 a shorter distance than the first arm 314. Since the counterweight 202 is heavier, such a shorter travel may exert the same or similar moment to balance changes in the bending moment of the sled member 104.

Figure 4A:
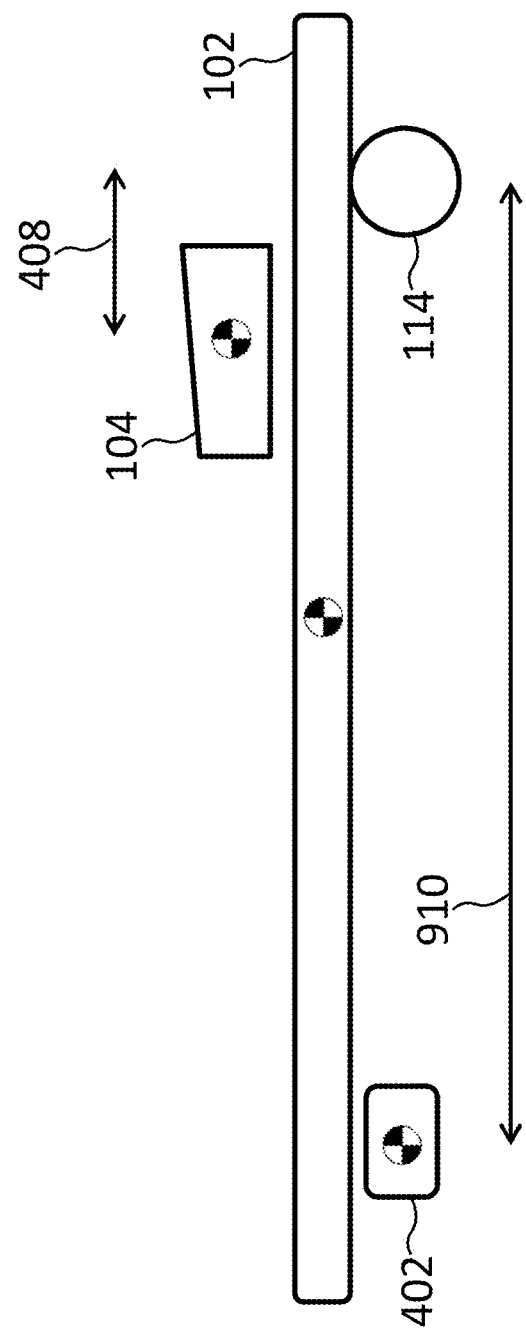

FIGS. 4A-4C illustrate an alternate configuration in which the counterweight 402 is configured to maintain a constant bending moment on the same side of the support structure 114, rather than balancing against the moment applied by sled member 104 on an opposite side of the support structure 114. In this configuration the sled base 102 may be attached to a support structure 114 at a position removed from a center point of the sled base 102. The total bending moment or torque exerted on the support structure 114 (i.e., the sum of the moment of the counterweight 402, the moment of the sled member 104, and the moment of the sled base 102) may be kept constant by moving the counterweight 202 back as the sled member 104 advances as illustrated in FIGS. 4*b* and 4C. In this configuration, counterweight 402 may be moved in response to movement of the sled member 104 by one or more pulleys, gears or other devices to control movement similar to the embodiments illustrated in FIGS. 3A through 3D.

In a further embodiment, a counterweight may be moved by a drive system (e.g., an electric motor) controlled by a control system in response to sensors that detect a need for balancing. For example, one or more sensors may detect weight, pressure, bending stress, strain, deflection of the sled base or other parameters of one or more components of the catheter positioning system. Based on data from of the sensors, the control system may reposition the counterweight accordingly to adjust the magnitude of force applied to the system by the counterweight. The control system may continue making adjustments based on feedback from the sensors until the desired state (e.g., a balanced total moment, zero total moment, a desired steady state response, etc.) is achieved.

Figure 5:
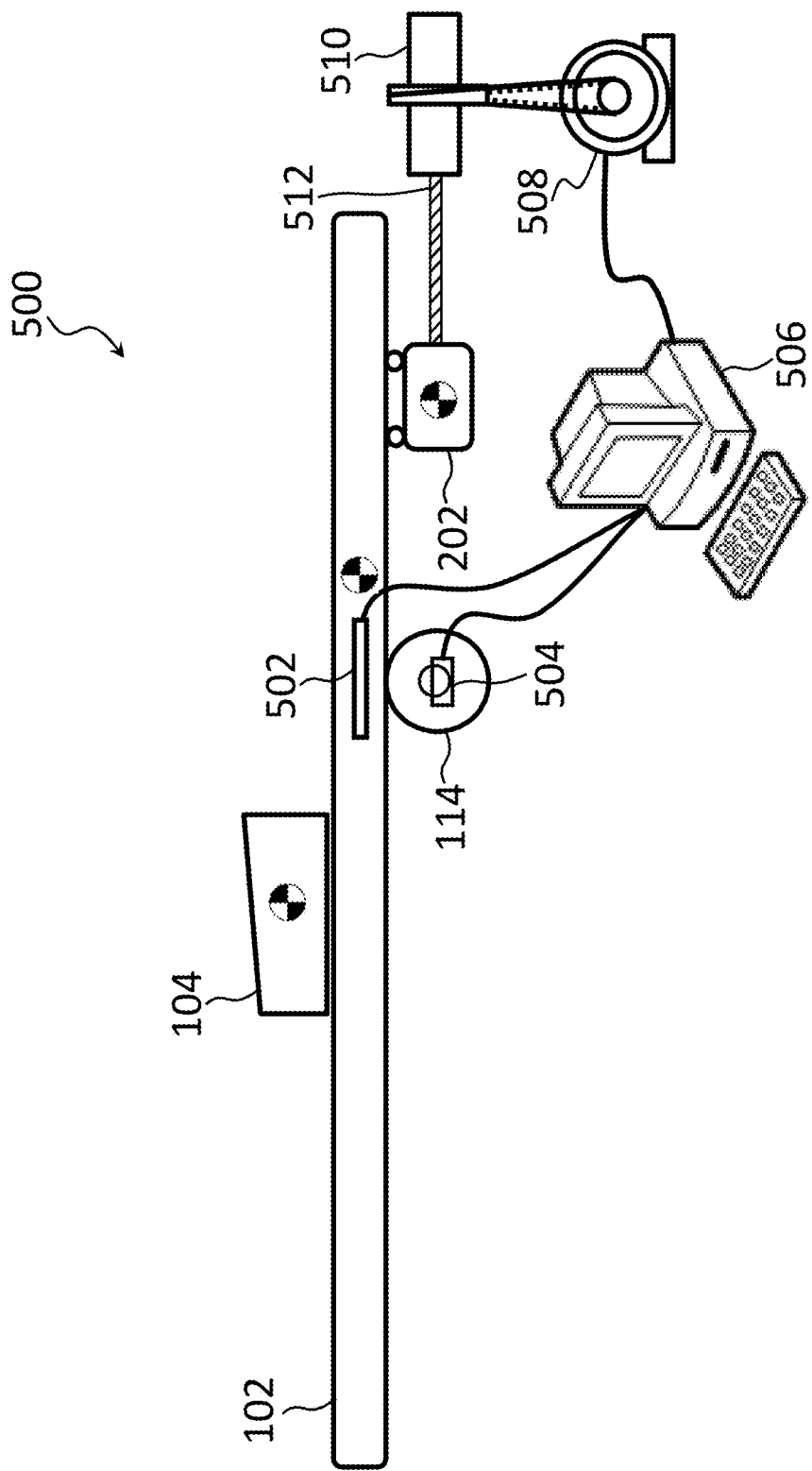
FIG. 5 is a system diagram illustrating an embodiment system with a counterweight and drive assembly controlled by a control system based on sensor inputs.

Such an embodiment is illustrated in FIG. 5. A catheter positioning system 500 may include a level sensor 502 and a stress sensor 504 coupled to a control system 506 that controls a counterweight drive mechanism 508, 510, 512. In this example embodiment, a stress sensor 504 capable of detecting when a bending stress is applied to the support structure 114 and/or a level sensor 502 capable of detecting when the sled base 102 is beginning to change its angle of orientation provide sensor data into a control system 506. The control system 506 may include a processor configured with processor executable instructions or hardwired control logic to generate a control signal for a drive motor 508 that is configured to reposition the counterweight 202 in order to compensate for the detected bending stress or tilt of the sled base 102. In the illustrated example, control signals from the control system 506 cause the drive motor 508 to turn a lead screw nut 510 to advance or retract a lead screw 512 coupled to the counterweight 202; however, any of a variety of drive mechanisms (e.g., wires and pulleys, linear actuators, a motor and drive gear on the counterweight, etc.) may be used in various embodiments.

In various embodiments, one or more damping systems may be used to stabilize the catheter positioning system. The damping systems may resist motion of the catheter positioning system, thereby preventing any sudden or jerky movements of the sled base, nose cone, or introducer that may cause deflections and interfere with catheter positioning procedures. Damping systems may help counter movement even when the sled member and counterweight are stationary, such as by resisting unintentional movement from bumps or snags.

Figure 6A:
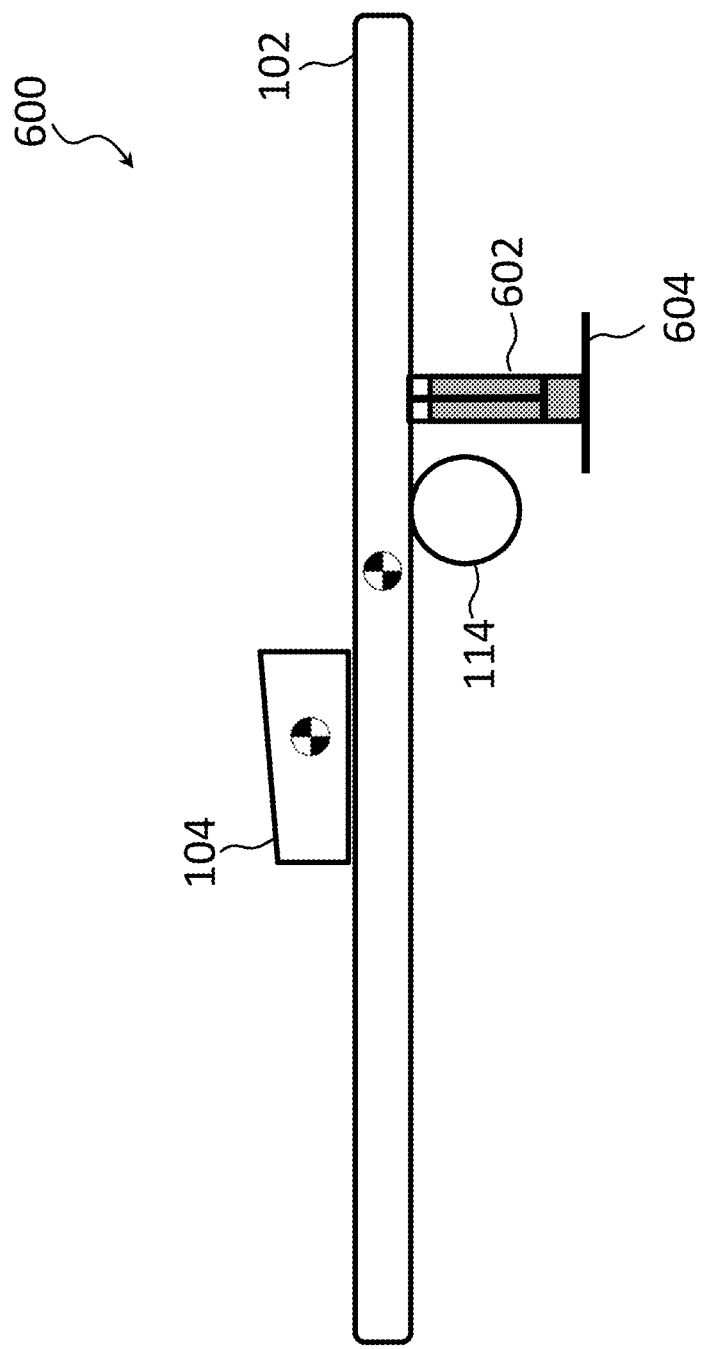
FIG. 6A is a system diagram illustrating an embodiment system with a passive damping system.

In various embodiments a passive damping system may include one or more shock absorbers or dashpots. For example, FIG. 6A illustrates an embodiment system 600 with a passive damping system 602 illustrated as a dashpot. The passive damping system 602 may be coupled to the sled base 102 and a secure surface 604, such as the operating table 120, the floor, or any other surface that will remain stationary during the operation and can resist any forces applied to it by the damping system 602 as the damping system resists motion by the sled base 102. The passive damping system 602 shown in FIG. 6A is linear and directly opposes deflection of the sled base 102. In alternate embodiments the passive damping system may be a rotational passive damping system configured to resist rotation of the sled base 102 about the support structure 114. Combinations of linear and rotational passive damping systems may also be used.

Alternate embodiments include active damping systems featuring motion compensating mechanisms coupled to a control system with sensors. FIG. 6B illustrates an embodiment catheter positioning system 650 with an active damping system 652 securely coupled to a base or surface 604, such as a secure mounting surface. The active damping system 652 may be or may include a linear actuator or motor, a rotational actuator or motor, a piezoelectric device, or other electromechanical transducer configured to apply a force to the sled base 102 (or other structure) to resist motions. The active damping system 652 may be controlled by a control system 506 configured to receive movement sensor data from a stress sensor 504 and a level sensor 502, for example. The control system 506 may include a processor configured with processor executable instructions or hardwired control logic to generate control signals for the active damping system 652 in response to motion/movement sensor data, with the control signals configured to cause the active damping system 652 to push or pull in the opposite direction of any motion/movement detected by the sensors 502, 504. The active damping system 652 is shown in FIG. 6B as a linear actuator that directly opposes deflection of the sled base 102. However, in alternate embodiments the active damping system 652 may be a rotational active damping system, such as a rotational actuator configured to resist rotation of the sled base 102 about the support structure 114. Combinations of linear and rotational active damping systems may also be used.

While various embodiments, including preferred embodiments, have been described, the invention is only limited by the scope of the claims. Those skilled in the art will recognize that the methods and systems of the present invention have many applications, may be implemented in many manners and, as such, is not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A catheter positioning system, comprising:
a sled member configured to accept a handle of a catheter;
a sled base configured to move the sled member along a length of the sled base in order to position the catheter within a patient;
a counterweight moveably coupled to the sled base; and
a drive mechanism coupled to the counterweight configured to move the counterweight in order to reduce shifting of a center of mass of the sled member, sled base and counterweigh as the sled member is moved along the sled base, wherein the counterweight has a weight substantially similar to that of the sled member and the drive mechanism is configured so that the counterweight moves the same distance as the sled member.

2. The catheter positioning system of claim 1, wherein the counterweight is moveably coupled to the sled base and the drive mechanism is configured so that the counterweight moves along the length of the sled base.

3. The catheter positioning system of claim 2, wherein the drive mechanism comprises a cable coupled between the counterweight and the sled member and passing around at least one pulley configured so that the counterweight moves in a direction opposite to that of the sled member.

4. The catheter positioning system of claim 1, wherein the drive mechanism comprises a drive motor and at least one gear coupled to the drive motor.

5. The catheter positioning system of claim 1, further comprising:
a sensor coupled to the catheter positioning system; and
a control system coupled to the sensor and configured to control the drive mechanism to move the counterweight based on data from the sensor.

6. The catheter positioning system of claim 5, wherein the sensor comprises at least one of a tilt sensor, a pressure sensor, a stress sensor, and a strain sensor.

7. The catheter positioning system of claim 5, further comprising an active damping system coupled with the control system, and wherein the control system is configured to control the active damping system based on data from the sensor.

8. The catheter positioning system of claim 1, wherein the counterweight is configured on the catheter positioning system to move in response to movements of the sled member so that a bending moment applied to a support structure supporting the sled base remains approximately constant.

9. The catheter positioning system of claim 1, further comprising a passive damping system.

* * * * *